US00PP20990P2

(12) United States Plant Patent
van Kleinwee

(10) Patent No.: US PP20,990 P2
(45) Date of Patent: May 11, 2010

(54) *OSTEOSPERMUM* PLANT NAMED 'OSECTRADEPU'

(50) Latin Name: *Osteospermum ecklonis*
Varietal Denomination: Osectradepu

(75) Inventor: Theodorus Cornelis Maria van Kleinwee, Hoorn (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/321,834

(22) Filed: Jan. 26, 2009

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent L Bell
(74) *Attorney, Agent, or Firm*—S. Matthew Edwards

(57) ABSTRACT

A new *Osteospermum* plant named 'Osectradepu' particularly distinguished by its trailing, very vigorous growth habit, its deep purple colored flowers, facing upwards and its strong heat tolerance.

1 Drawing Sheet

Latin name of the genus and species of the plant claimed: *Osteospermum ecklonis.*

Varietal denomination: 'Osectradepu'.

BACKGROUND OF THE NEW PLANT

The present invention relates to a new and distinct cultivar of *Osteospermum* plant, botanically known as *Osteospermum ecklonis*. The new *Osteospermum* is propagated by cuttings resulting from an open pollination of a proprietary *Osteospermum ecklonis* seedling selection as the female, or seed, parent identified as 'F0264-2' (not patented). This pollination took place in Enkhuizen, Netherlands in 2004.

The new *Osteospermum* was discovered and selected as a single flowering plant within the progeny of the stated population grown in Enkhuizen, The Netherlands in 2005. The new *Osteospermum* plant has been repeatably asexually reproduced by cuttings in Enkhuizen, The Netherlands since 2005. The distinctive characteristics of this new *Osteospermum* plant are stable and reproduced true to type in successive generations.

DESCRIPTION OF THE DRAWING

This new *Osteospermum* plant is illustrated by the accompanying photographic drawing which shows blooms, buds and foliage of the plant in full color, the color shown being as true as can be reasonably obtained by conventional photographic procedures.

SUMMARY OF THE INVENTION

Plants of the cultivar 'Osectradepu' have not been observed under all possible environmental conditions. The phenotype may vary with variations in environment such as temperature and light intensity without, however, any variance in genotype.

The following traits have been repeatedly observed and are determined to be the unique characteristics of 'Osectradepu.' These characteristics in combination distinguish 'Osectradepu' as a new and distinct cultivar:

1. Trailing plant habit
2. Strong vigor
3. Deep purple colored flowers, facing upwards
4. Strong heat tolerance In side-by-side comparisons conducted in Enkhuizen, The Netherlands, plants of the new *Osteospermum* differed from plants of the female parent selection in the following characteristics:

1. Plants of the new *Osteospermum* are more trailing than plants of the female parent.
2. Plants of the new *Osteospermum* are more vigorous than plants of the female parent.
3. The flower color of plants of the new *Osteospermum* is deeper purple than the flower color of plants of the female parent.

TABLE 1

DIFFERENCES BETWEEN THE NEW CULTIVAR 'OSECTRADEPU' AND TWO SIMILAR CULTIVARS

| | 'Osectradepu' | 'Oslalipu' (U.S. Plant Pat. No. 18,873) | 'Osoutis' (U.S. Plant Pat. No. 15,491) |
|---|---|---|---|
| Plant vigour | Very strong | Moderate | Moderate |
| Plant habit | Trailing | Trailing | Upright |
| Ray floret color | RHS N78A | RHS 77C | RHS N78A |

DESCRIPTION OF THE NEW CULTIVAR

The following detailed descriptions set forth the distinctive characteristics of this new *Osteospermum* plant. The data which define these characteristics were collected from asexual reproductions carried out in Enkhuizen, The Netherlands. The plant history was taken on 15 week old plants. The instant plant was grown indoors in a 10.5 cm container and transplanted into the open field in week 20.

Color references are primarily to The R.H.S. Colour Chart of the Royal Horticultural Society of London, edition 2001.

The plant:

*Classification — Botanical.*—*Osteospermum ecklonis.*

Parentage:

*Female parent.*—Proprietary seedling selection 'F0264-2', not patented.

*Male parent.*—Female is open pollinated so male is unknown.

Plant description:

*Growth habit.*—Round, trailing.

*Plant height.*—15 cm.

*Spreading area of plant.*—40 cm.

*Vigour.*—Very strong.

*Branching character.*—Freely branching, 12 lateral branches without pinching.

*Flowering period.*—From May until October.

The stem:

*Length.*—19 cm.

*Diameter.*—7 mm.

*Internode length.*—0.4 cm.

*Texture.*—Glabrous.

*Color.*—RHS 144A; older parts that are exposed to sunlight can show some anthocyanin spots, color N200A.

The foliage:

*Arrangement.*—Single, alternate.

*Shape.*—Elliptic.

*Apex.*—Broadly acute.

*Base.*—Attenuate.

*Margin.*—Irregularly serrated.

*Number of leaves per lateral branch.*—20–50.

*Texture.*—Glabrous, leathery.

*Color upper side.*—RHS 137B.

*Color lower side.*—RHS 137B.

*Length.*—First developed leaves: up to 8 cm; last developed leaves: up to 4 cm.

*Width.*—First developed leaves: up to 4 cm; last developed leaves: up to 1 cm.

*Petiole.*—Absent.

The inflorescence:

*Number of inflorescences per mature plant.*—50.

*Inflorescence bud.*—Shape: Ovoid. Length: 10 mm. Width: 10 mm. Color: RHS 144A.

*Inflorescence lastingness on the plant.*—Approximately 5 days, depending on temperature.

*Inflorescence diameter.*—45–50 mm.

*Inflorescence depth.*—9 mm.

*Disc diameter.*—9 mm.

*Fragrance.*—Absent.

*Disc florets.*—Shape: Tubular, elongated. Number of disc florets per inflorescence: 70. Length: 7 mm. Width: 1 mm. Apex: Five pointed. Color: RHS 91C; in young stage RHS 92A.

*Ray florets.*—Shape: Capitulum with two series of ray florets. Number of ray florets per inflorescence: 17. Color upper surface: N78A. Color lower surface N78A. Length: 25 mm. Width: 6 mm. Apex: Rounded. Base: Acute. Margin: Entire. Texture: Satiny.

*Peduncles.*—Length: 1–7 cm. Texture: Sturdy; tiny hairs. Color: RHS 144A. Diameter: 1.5 mm. Shape: Round.

*Phyllaries.*—Texture: Rough; tiny hairs. Number of phyllaries: 16. Color: RHS 143A. Length: 10 mm. Margin: Entire. Width: 1 mm. Apex: Acute. Shape: Ligulate.

Reproductive organs:

*Androecium.*—Presence: Present on disc florets only. Shape: Oblong; five stamens fused to one. Length: 3 mm. Width: 1 mm. Pollen color: RHS 25A.

*Gynoecium.*—Presence: Present on both ray and disc florets. Pistil number: One pistil per ray or disc floret. Pistil length: 4 mm. Stigma color: RHS N187A. Stigma shape: Bipartite.

Seed development: Seed development has been observed on plants of the new *Osteospermum.*

*Amount of seeds produced.*—Moderate.

*Seed length.*—8 mm.

*Seed diameter.*—3 mm.

*Seed color.*—Mature seed RHS 200A; immature seed RHS 144A.

*Seed shape.*—Elliptic.

Disease and pest resistance: No disease and pest resistance has been observed to date.

What is claimed is:

1. A new and distinct variety of *Osteospermum* plant named 'Osectradepu' as substantially illustrated and described herein.

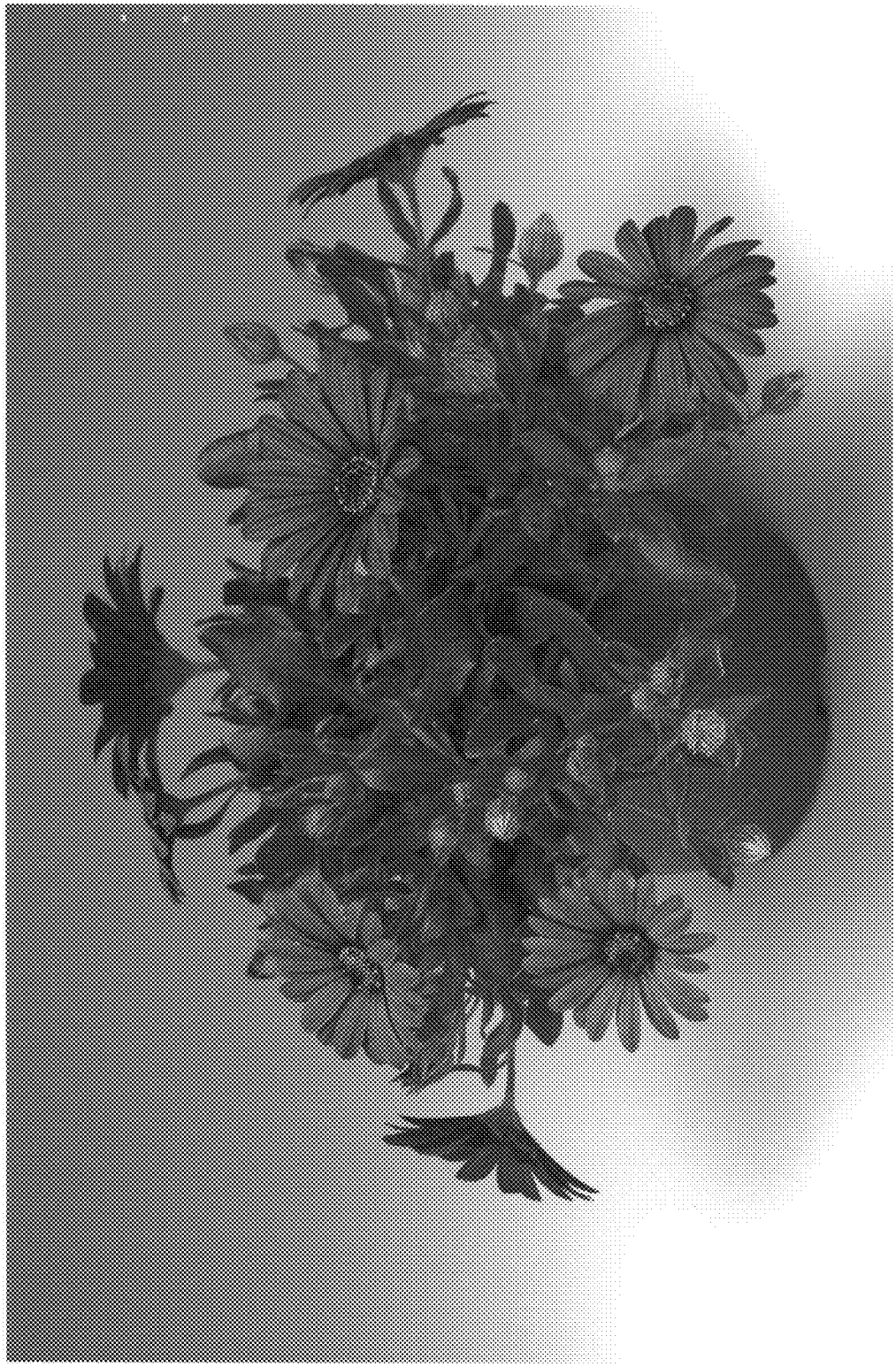

* * * * *